(12) United States Patent
Mistretta et al.

(10) Patent No.: US 7,812,006 B2
(45) Date of Patent: Oct. 12, 2010

(54) CONJUGATES OBTAINED BY REDUCTIVE AMINATION OF THE PNEUMOCOCCUS SEROTYPE 5 CAPSULAR POLYSACCHARIDE

(75) Inventors: Noëlle Mistretta, Sain Bel (FR); Emilie Danve, Tassin la Demi Lune (FR); Monique Moreau, Lyons (FR)

(73) Assignee: Aventis Pasteur S.A., Lyon (FR)

( * ) Notice: Subject to any disclaimer, the term of this patent is extended or adjusted under 35 U.S.C. 154(b) by 884 days.

(21) Appl. No.: 10/758,142

(22) Filed: Jan. 15, 2004

(65) Prior Publication Data

US 2004/0170638 A1    Sep. 2, 2004

Related U.S. Application Data

(60) Provisional application No. 60/442,154, filed on Jan. 22, 2003.

(30) Foreign Application Priority Data

Jan. 17, 2003    (FR)    .................................... 03 00488

(51) Int. Cl.
    *A61K 31/715*    (2006.01)
    *C08B 37/00*    (2006.01)
    *C07H 5/04*    (2006.01)
    *C07H 5/06*    (2006.01)
    *C12P 19/04*    (2006.01)

(52) U.S. Cl. .......................... 514/54; 536/55.1; 536/123

(58) Field of Classification Search ................ 536/23.7, 536/123.1, 124, 123.12, 120, 26.1; 514/2, 514/8, 53, 21, 23, 54; 424/194.1, 244.1, 424/184.1, 197.11, 234.1, 190.1, 450; 428/474.4; 510/441

See application file for complete search history.

(56) References Cited

U.S. PATENT DOCUMENTS

| 4,761,283 | A | * | 8/1988 | Anderson | ................. | 424/194.1 |
| 6,045,805 | A | | 4/2000 | Moreau | | |
| 6,596,861 | B1 | * | 7/2003 | Moreau | .................... | 536/123.1 |

FOREIGN PATENT DOCUMENTS

| EP | 0 245 045 A2 | 11/1987 |
| EP | 0 477 508 A1 | 1/1992 |
| EP | 0 562 107 B1 | 9/1993 |
| WO | WO 94/29339 | 12/1994 |
| WO | WO 98/51339 | 11/1998 |
| WO | WO 00/55210 | 9/2000 |
| WO | WO 00/56358 A2 | 9/2000 |

OTHER PUBLICATIONS

Jansson et al. "Structural studies of the capsular polysaccharide from *Streptococcus pneumoniae* Type 5." Carbohydrate Research, 140, 101-110, 1985.*
Pinta et al., 2009, Chem. Eur. J., 15, 9747-9754, Identification and Role of a 6-Deoxy-4-Keto-Hexosamine in the Lipopolysaccharide Outer Core of *Yersinia enterocolitica* Serotype O:3.
Jansson, Per-Erik et al., "Structural Studies of the Capsular Polysaccharide From *Streptococcus pneumoniae* Type 5," Carbohydrate Research, 140 (1985), pp. 101-110.
Gotschlich, Emil C. et al., "Human Immunity to the Meningococcus, III. Preparation and Immunochemical Properties of the Group A, Group B, and Group C Meningococcal Polysaccharides", Journal of Exp. Med., 129 (1969) 1349-1365.
Jones, Christopher et al., "Full Assignment of the Proton and Carbon NMR Spectra and Revised Structure for the Capsular Polysaccharide from *Streptococcus pneumoniae* Type 17F", Carbohydrate Research, 325 (2000) 192-201.
Del Guercio, Marie-France et al., "Potent Immunogenic Short Linear Peptide Constructs Composed of B Cell Epitopes and Pan DR T Helper Epitopes (PADRE) for Antibody Responses In Vivo", Vaccine, vol. 15, No. 4, (1997) pp. 441-448.
Laferriere, Craig A., et al., "The Synthesis of *Streptococcus pneumonia* Polysaccharide—Tetanus Toxoid Conjugates and the Effect of Chain Length On Immunogenicity," Vaccine, vol. 15, No. 2 (1997) pp. 179-186.

* cited by examiner

*Primary Examiner*—Eric S Olson
(74) *Attorney, Agent, or Firm*—McDonnell Boehnen Hulbert & Berghoff LLP

(57) ABSTRACT

The invention relates to conjugates derived from the reductive amination of the pneumococcus serotype 5 capsular polysaccharide. The conditions for reductive amination differ from conventional conditions in that they make it possible to avoid the appearance of an undesirable compound which harms the immunogenicity of the conjugates. In carbon NMR spectrum, this undesirable compound is characterized by a resonance signal between 13 and 14 ppm. The aminated polysaccharides used to produce the conjugates therefore have a carbon NMR spectrum lacking a resonance signal between 13 and 14 ppm. The invention offers two conditions for reductive amination. According to a first method, the reductive amination is carried out at a slightly acidic pH (4-6.5) for at the very most 4 hours. According to a second method, the polysaccharide is first of all reduced, then fragmented and, finally, subjected to a reductive amination per se, under conditions which may or may not be conventional. Depending on the method used, the structure of the aminated polysaccharide may vary (conversion or not of the Sug residue of the repeating unit to N-acetylated quinovosamine and to N-acetylated fucosamine); however, these variations, as recorded in carbon NMR spectrometry, have no effect on the immunogenicity.

12 Claims, 2 Drawing Sheets

Figure 1:
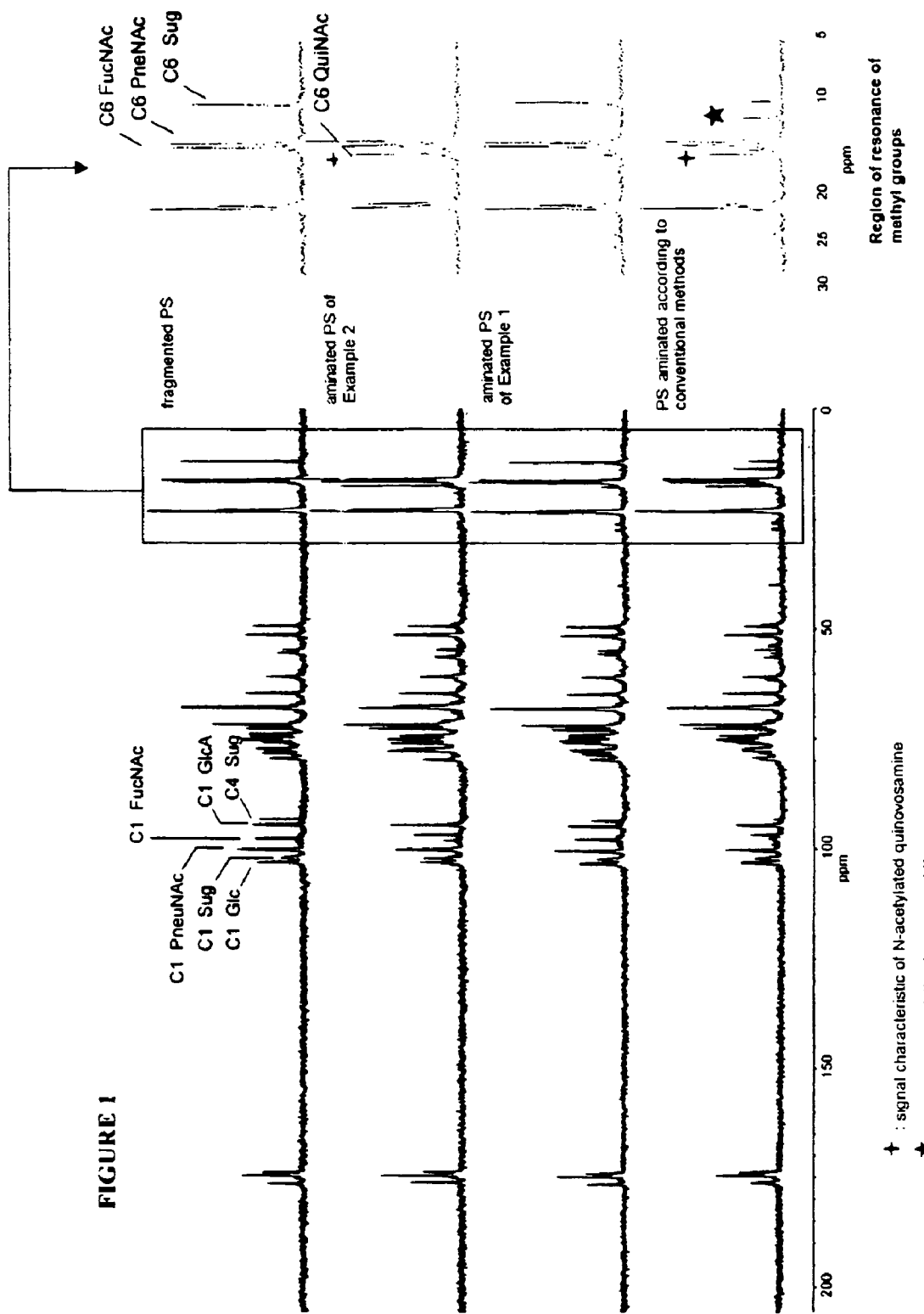

Chromatograms of HPAE-PAD, on a CarboPac PA 10 column, of the pneumococcus type 5 polysaccharide (Pn5) after hydrolysis with TFA FucN = fucosamine
X = compound X
GlcA = glucuronic acid
GlcA-FucN = glucuronic acid-fucosamine disaccharide QuiN = quinovosamine
PneN = pneumosamine

CONJUGATES OBTAINED BY REDUCTIVE AMINATION OF THE PNEUMOCOCCUS SEROTYPE 5 CAPSULAR POLYSACCHARIDE

This application claims the benefit of the United States Provisional Patent Application No. 60/442,154, filed on Jan. 22, 2003 and of French Application No. 0300488, filed Jan. 17, 2003.

The present invention relates especially to a particular aminated form of the pneumococcus type 5 capsular polysaccharide, to the conjugates incorporating this form and also to the methods of production for obtaining it.

Pneumococcus (*Streptococcus pneumoniae*) is a Gram-positive encapsulated bacterium responsible for meningitis and bacteremia. It also causes a large number of the respiratory infections such as bronchitis, rhinitis or otitis with complications in adults and in children. Pneumococci are divided into serotypes according to the structure of the polysaccharides which form the capsule. The serotyping of pneumococci is carried out using a battery of immune sera, each immune serum being specific for a single type of capsular polysaccharide. More than 90 different serotypes, all pathogenic to humans, have been registered. Serotypes 6B, 14, 18C, 19F and 23F are prevalent in young children and cause pneumonia and otitis. Serotypes 1 and 5 are encountered more commonly in developing countries than in industrialized countries.

Vaccines which protect against the main serotypes encountered clinically in humans have been developed or are undergoing development. A vaccine comprising the capsular polysaccharides of 23 different serotypes responsible for 90% of pneumococcal infections (1, 2, 3, 4, 5, 6B, 7F, 8, 9N, 9V, 10A, 11A, 12F, 14, 15B, 17F, 18C, 19A, 19F, 20, 22F, 23F, 33F) is effective in adults and children over the age of two. On the other hand, children under the age of two, due to the immaturity of their immune system, do not respond to this vaccine consisting of T-independent polysaccharide antigens. This obstacle has been overcome by developing vaccines containing capsular polysaccharides of various pneumococcal serotypes coupled (conjugated) to one or more carrier proteins (WO 98/51339). These conjugates induce the development of a T-dependent protective humoral immunity in young children, resulting in the production of specific antibodies against the polysaccharides of the various serotypes used in these conjugates.

The capsular polysaccharides of the various serotypes of pneumococcus are all made up of a repeating base unit (repeating unit) consisting of several sugars. By way of illustration, it is indicated that the base unit of the pneumococcus type 5 polysaccharide consists of 5 hexoses: glucose, N-acetylated fucosamine, N-acetylated pneumosamine (2-acetamido-2,6-deoxytalose), glucuronic acid and a sugar called Sug (2-acetamido-2,6-deoxyhexose-4-ulose) linked to one another to form a chemical structure with the following condensed formula:

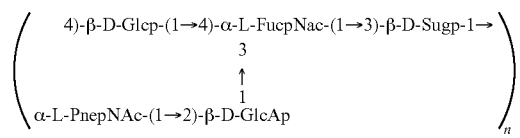

The expanded formula which corresponds thereto is formula (I) as below:

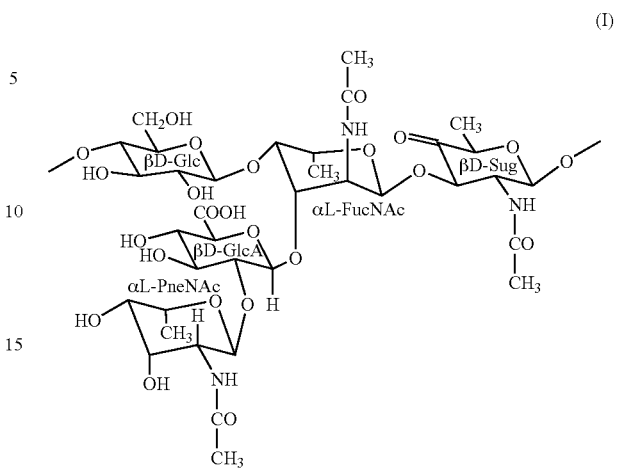

in which Sug signifies 2-acetamido-2,6-deoxyhexose-4-ulose; PneNAc signifies 2-acetamido-2,6-deoxytalose, also called N-acetylated pneumosamine; FucNAc signifies 2-acetamido-2,6-deoxygalactose, also called N-acetylated fucosamine; GlcA signifies glucuronic acid; and Glc signifies glucose.

This formula was provided by P. E. Jannson et al., Carbohydrate Research (1985) 140 (1): 101. However, it is not impossible for a small percentage of the repeating units of the polysaccharide to have a hydroxyl group in place of the ketone function.

Many methods exist for coupling a polysaccharide to a carrier protein. Among these, methods which involve, in a preliminary manner, reductive amination of the polysaccharide are commonly used. For example, as described in EP 562 107, the polysaccharide is first of all coupled by reductive amination to a bifunctional spacer of the $NH_2$—R—$NH_2$ type, and then the polysaccharide thus derivatized and aminated is coupled to a bifunctional linking agent in particular capable of reacting with an amine function. The polysaccharide thus activated is then conjugated to a carrier protein. According to other variants, it is also possible to couple the polysaccharide directly to the protein by reductive amination, or even to omit the spacer.

As is well known, a reductive amination reaction takes place in two steps. In a first step, an intermediate compound, called Schiff base, of formula R—CH=$NH^+$—R', forms resulting from the interaction between an aldehyde group of a first molecule (R—CHO) and a primary amine group (R'—$NH_2$) of a second molecule. The Schiff base is then reduced in a second step in the form of an amino compound R—$CH_2$—NH—R' in the presence of a reducing agent. Use is made of a selective reducing agent capable of specifically reducing the imine function of the Schiff base, such as a hydrogen activated by catalyst, sodium cyanoborohydride ($NaCNBH_3$) or an amine borane. Cyanoborohydride or pyridine borane is preferably used.

Since all the polysaccharides have an aldehyde function at the end of the chain (terminal aldehyde function), the conjugation methods comprising a reductive amination of the polysaccharide can be applied very generally and, when there is no other aldehyde function in the repeating unit (intrachain aldehyde function), such methods make it possible to obtain conjugates in which a polysaccharide molecule is coupled to a single molecule of carrier protein.

In an entirely conventional manner, a polysaccharide is subjected to a reductive amination, in the presence of a reducing agent selective for the Schiff base, for at least 24 to 48 hours, at a neutral or basic pH.

Thus, U.S. Pat. No. 4,761,283 describes the reductive amination of the pneumococcus type 6A capsular polysaccharide (prefragmented by acid hydrolysis) with a nontoxic mutant of diphtheria toxin (mutant CRM 197), in the presence of sodium cyanoborohydride. The pH of the reaction medium is basic (pH=8) and the incubation period is 18 days at 37° C.

EP 477 508 describes the reductive amination of pneumococcus type 6A, 14, 19F and 23F polysaccharides with diaminomethane or diaminoethane, in the presence of pyridine borane, which plays the role of reducing agent for the Schiff base. The pH of the reaction medium is 9.2. The reaction takes place for 48 hours.

In EP 562 107 mentioned above, the reductive amination of the polysaccharide is carried out at pH 8 for 6 days.

Since the pneumococcus type 5 capsular polysaccharide comprises an intrachain ketone function, it should theoretically be expected that this ketone function, in addition to the terminal aldehyde function, be amino- reduced during the reductive amination of the polysaccharide. Now, when the pneumococcus type 5 capsular polysaccharide and a capsular polysaccharide of another serotype or of another species not comprising any intrachain aldehyde and ketone functions are subjected to the amination in parallel, the degrees of amination are equivalent, which clearly appears to confirm that only the terminal aldehyde function of the pneumococcus type 5 capsular polysaccharide is aminated and that only this function is modified during the reaction. Now, in truth, this is not the case.

In fact, it is has now been discovered that the chemical structure of the repeating unit of the pneumococcus type 5 polysaccharide is modified after reductive amination according to the conventional method. This has been shown by nuclear magnetic resonance (NMR) spectrometry and by high performance anion-exchange chromatography coupled to pulsed amperometric detection (HPAEC-PAD chromatography). The vast majority of the Sug residue disappears in favor of three new compounds: (i) N-acetylated β-D-quinovosamine derived from reduction of the ketone function of the Sug residue to an alcohol function and (ii) a compound X resulting from a more considerable conversion of the Sug residue. The third compound is none other than the isomer of the N-acetylated β-D-quinovosamine, i.e. N-acetylated β-D-fucosamine, also derived from reduction of the Sug residue, and for which a slight increase is observed.

In NMR spectrometry and as shown in FIG. 1, the pneumococcus type 5 polysaccharide in its simply fragmented native form exhibits, in the resonance region for the carbons of methyl groups at position 6 (C6) of sugars, the three resonance signals characteristic of the methyl groups of N-acetylated pneumosamine (PneNAc), of N-acetylated fucosamine (FucNAc) and of the Sug residue (FIG. 1-*spectrum* 1). The fragmentation does not in any way modify the spectrum, but improves the resolution thereof. After conventional amination with diaminohexane, in the presence of sodium cyanoborohydride (NaCNBH$_3$), it is noted that the resonance signal characteristic of the methyl group of the Sug residue (abbreviated to "signal characteristic of the Sug residue") is substantially decreased and this decrease is accompanied by the appearance of two new resonance signals: one between 17 and 18 ppm, characteristic of N-acetylated quinovosamine (QuiNAc) and the other between 13 and 14 ppm, which denotes a new compound, the structure of which is unknown and which, for this reason, is named compound X (FIG. 1-*spectrum* 4).

Figure 2:
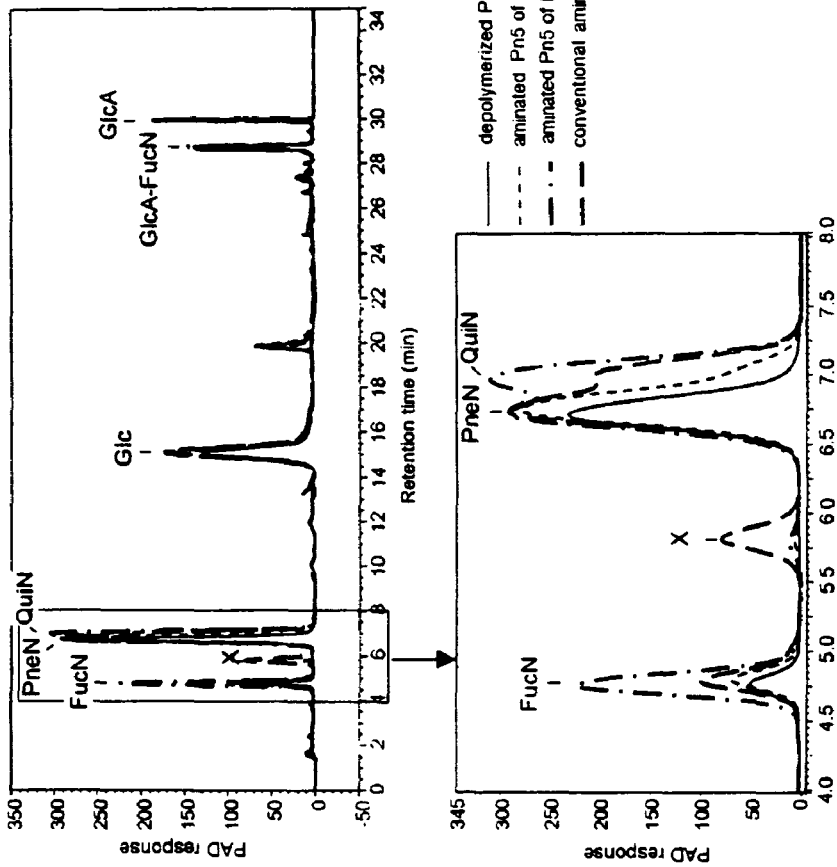

In HPAEC-PAD chromatography, when the chromatograms for the products of hydrolysis with 2N trifluoroacetic acid, for 2 hours at 120° C., of the native or depolymerized polysaccharide and of the polysaccharide obtained after conventional reductive amination are compared, as shown in FIG. 2 (the dot-dashed curve), the appearance of a first peak (between 5.50 and 6.10 min when the chromatography is carried out under the conditions specified later) corresponding to a compound derived from the reductive amination, the structure of which is unidentified (compound X), and also a second peak (between 6.90 and 7.40 min when the chromatography is carried out under the conditions specified later) characteristic of quinovosamine is noted. In addition, the intensity of the peak corresponding to fucosamine is substantially increased. It should be noted that the chromatograms, including that of the native or depolymerized polysaccharide, comprise no peak corresponding to the Sug residue. Specifically, in order to be subjected to HPAEC-PAD chromatography, the polysaccharide must first of all be hydrolyzed. This hydrolysis destroys the Sug residue; it also has the effect of converting QuiNAc, PneNAc and FucNAc to quinovosamine (QuiN), pneumosamine (PneN) and fucosamine (FucN).

In addition, it was discovered that conversion of the Sug compound to compound X was harmful to the immunogenicity of the polysaccharide, even though this conversion is only partial—that is to say taking place only in some of the repeating units of the polysaccharide and not in all of them. On the other hand, the QuiNAc or FucNAc conversion has no notable influence.

It therefore appeared to be desirable to investigate means which made it possible to avoid the appearance of the compound X. This was made possible by modifying the conventional procedure for reductive amination. In an alternative manner, it is also possible to reduce the ketone functions (C=O) of the native (nonfragmented) polysaccharide beforehand. This can be carried out using a strong reducing agent such as NaBH$_4$. This reducing agent does not generate any undesirable compound. It reduces only the ketone and aldehyde functions. However, since it reduces these functions, it is then necessary to fragment the reduced polysaccharide in order to reintroduce terminal aldehyde groups. The reduction of the ketone functions prevents any subsequent modification when the polysaccharide is then subjected to any reductive amination.

For this reason, a subject of the invention is:
(i) A pnemococcus type 5 capsular polysaccharide which is aminated on the terminal aldehyde group and which exhibits (i) a carbon ($^{13}$C) NMR spectrum lacking a resonance signal between 13 and 14 ppm inclusive; (ii) an HPAEC-PAD chromatogram substantially lacking a peak between the fucosamine and pneumosamine peaks, the chromatogram being obtained by elution, from a Carbopac™ PA10 column, in an 18 mM sodium hydroxide solution, at a flow rate of 1 ml/min for 15 min, of the monosaccharides derived from the hydrolysis of said polysaccharide; or (iii) both.
(ii) A conjugate in which the polysaccharide according to the invention is coupled to a carrier polypeptide (P).
(iii) A first method for producing an aminated pneumococcus type 5 capsular polysaccharide, according to which the polysaccharide is subjected to a reductive amination in the presence of a reducing agent selective for a Schiff base, at a pH of 4 to 6.5, preferably of 5 to 6, for a period not exceeding 4 hours.

(iv) A second method for producing an aminated pneumococcus type 5 capsular polysaccharide, according to which (i) the polysaccharide is reacted with an agent capable of reducing a ketone function, (ii) the reduced polysaccharide obtained in (i) is fragmented, and (iii) the reduced and fragmented polysaccharide is subjected to a reductive amination.

In the remainder of the text, the term "aminated polysaccharide" refers to a pneumococcus type 5 capsular polysaccharide which is aminated on the terminal aldehyde group; that is to say derived from the reaction of the terminal aldehyde function with an amine function.

The reductive amination of a polysaccharide can be carried out by reacting the terminal aldehyde function of a polysaccharide with compounds which are very diverse but of course all characterized in that they have at least one primary amine function. These compounds may be polypeptides or chemical compounds. These polypeptides and these chemical compounds will be mentioned in greater detail in the subsequent description. When a polypeptide is involved, the product of the reductive amination is in fact a polysaccharide-polypeptide conjugate.

For use in the methods according to the invention, a pneumococcus type 5 capsular polysaccharide is advantageously pre-purified from a bacterial culture, for example according to the method of Gotschlich et al., J. Exp. Med. (1969) 129: 1349.

The polysaccharide may be used unmodified (reference is then made to native form) or else fragmented. In fact, the size of the polysaccharide is absolutely not critical. In its native form, the polysaccharide contains approximately 300 repeating units. A fragmented polysaccharide may consist of at least 4 repeating units, in general from 25 to 100 repeating units. If necessary, the size of a polysaccharide can be determined according to known methods, for example by determining its KD by gel filtration or by measuring its molecular mass by SEC-triple detection (exclusion-diffusion chromatography coupled with triple detection: refractometry, viscosimetry, light scattering).

A polysaccharide can be fragmented according to various methods known to those skilled in the art, for example by controlled acid or basic hydrolysis or oxidative free-radical depolymerization as described in EP 562 107.

In the first method according to the invention, a fragmented polysaccharide is preferably used; in the second, a native polysaccharide.

In order to characterize the present invention, nuclear magnetic resonance (NMR) spectrometry can be used according to entirely conventional protocols; in particular, the data can be collected using any type of device intended for this purpose. Carbon NMR spectrometry has already been widely used to study the repeating units of a certain number of capsular polysaccharides, in particular those of pneumococcus. By way of example, mention is made of C. Jones et al., Carbohyd. Res. (2000) 325: 192. Those skilled in the art in the field of spectral analysis therefore have sufficient information to carry out for themselves the analysis of the type 5 polysaccharide by carbon NMR spectrometry.

However, by way of example, a protocol for preparing the samples is indicated, which is in particular suitable for subsequent measurement in a Bruker DRX500 spectrophotometer with a broadband measuring probe (spectral width: 27500 Hz). 12 to 17 mg of a lyophilizate of a type 5 polysaccharide are dissolved in 0.5 ml of heavy water ($D_2O$). This sample is placed in a 5 mm tube specially designed for NMR analysis. The spectra are then recorded at 70° C. (343 K).

For the purposes of characterization, the HPAEC-PAD chromatography should be carried out under very precise conditions regarding the type of column, the elution solutions and the elution flow rate. A complete procedure is provided below.

The aminated polysaccharides should first of all be hydrolyzed to monosaccharides. To do this, 5 to 20 µg of aminated polysaccharide in solution in deionized water at a concentration of 10-40 µg/ml are treated with 500 µl of 2N trifluoroacetic acid for 2 hours at 120° C. in a hermetically stoppered flask. The hydrolysates are dried under a stream of nitrogen at 40° C. so as to remove the trifluoroacetic acid. The residues are then dissolved in 400 µl of deionized water.

The chromatography is carried out on a CarboPac™ PA10 analytical column (4×250 mm) marketed by Dionex. This column consists of a support based on polystyrene and sulfonated divinylbenzene having a degree of cross-linking of 55% covered with latex microbeads grafted with quaternary ammonium groups. The degree of crosslinking of the latex (latex microbeads) is 5%; the diameter of the microbeads is 400 nm.

5 µg of hydrolysate are injected into the column. The column is then subjected to a flow of an 18 mM sodium hydroxide solution for 15 min at a flow rate of 1 ml/min, in order to elute the uncharged monosaccharides and oligosaccharides such as hexoses and hexosamines. To finish off the chromatogram, it is possible to subsequently gradually increase the molarity of the sodium hydroxide solution up, to 100 mM and, finally, to elute the remaining acidic monosaccharides and oligosaccharides using a solution of 100 mM sodium hydroxide/300 mM sodium acetate. Throughout the entire elution, the flow rate is 1 ml/min and the temperature is 30° C.

Under these conditions, the distance between the fucosamine and pneumosamine peaks is approximately 2 min. When the fucosamine and pneumosamine peaks appear at 4.75 and 6.75 min respectively, the peak X, if it should appear, appears between 5.50 and 6.10 (5.80 min).

The products obtained using each of the two methods according to the invention both correspond to the definition of the product according to the invention, but differ with regard to the percentage of Sug compound and of N-acetylated quinovosamine.

When the first method according to the invention (which specifies optimized conditions for reductive amination) is used, an aminated polysaccharide is obtained which exhibits:
(i) a carbon NMR spectrum which comprises a resonance signal between 11.5 and 12.5 ppm, inclusive, characteristic of the Sug compound, and a resonance signal located between 17 and 18 ppm inclusive, characteristic of N-acetylated quinovosamine, the intensity of which is less in comparison with the signal located between 17 and 18 ppm, inclusive, in the ($^{13}C$) NMR spectrum of a pneumococcus type 5 capsular polysaccharide obtained after reductive amination, in the presence of sodium cyanoborohydride, at pH 8, for 48 hours; or
(ii) an HPAEC-PAD chromatogram which comprises a peak eluted immediately after the pneumosamine, characteristic of quinovosamine, the intensity of which is less in comparison with the equivalent peak in the HPAEC-PAD chromatogram of a pneumococcus type 5 capsular polysaccharide obtained after reductive amination, in the presence of sodium cyanoborohydride, at pH 8, for 48 hours; or
(iii) both.

It is not possible to quantify in absolute terms the percentage of Sug residues which had been modified after reductive amination, in a polysaccharide molecule taken separately or in a set of molecules. On the other hand, it is possible to indicate that the degree of modification of the Sug residues is decreased by at least 65%—when it is not by at least 70 or 75%—when the pneumococcus type 5 capsular polysaccharide is obtained in aminated form using the first method according to the invention, in comparison with a pneumococcus type 5 capsular polysaccharide aminated according to a conventional method. After reductive amination according to the first method according to the invention, most of the modifications which persist relate to the conversion of certain Sug residues of the polysaccharide to N-acetylated quinovosamine; the compound X is not substantially formed, as reflected by the carbon NMR spectrum and the HPAEC-PAD chromatogram (FIG. 1—2nd spectrum and FIG. 2—dashed curve). Specifically, the spectrum exhibits no resonance signal between 13 and 14 ppm inclusive, characteristic of the compound X, and the chromatogram simply exhibits a broad peak of very low intensity between the fucosamine and pneumosamine peak (between 5.50 and 6.10 min).

Using the first method according to the invention, it is even possible to obtain an aminated polysaccharide which exhibits (i) a carbon NMR spectrum definitely lacking a resonance signal between 17 and 18 ppm; (ii) an HPAEC-PAD chromatogram lacking a quinovosamine peak (between 6.90 and 7.40 min), the peak observed with the polysaccharide aminated according to a conventional amination method being reduced so as to be no more than a simple shoulder of the preceding peak (pneumosamine peak); or (iii) both.

The second method according to the invention requires the prior reduction of the ketone groups of the native polysaccharide. Under these conditions, it is readily understood that the Sug residues are essentially converted to N-acetylated fucosamine and quinovosamine. In that case, reference is made to a "reduced polysaccharide". Reductive amination according to a conventional procedure of the reduced and fragmented polysaccharide has no notable effect on the structure of the repeating units. This is clearly shown in FIG. 2—curve with dashes and dots.

Thus, when the second method according to the invention is used, an aminated polysaccharide is obtained which exhibits:
(i) a carbon NMR spectrum lacking a resonance signal between 11.5 and 12.5 ppm, inclusive, characteristic of the Sug compound, which comprises a resonance signal located between 17 and 18 ppm inclusive, characteristic of N-acetylated quinovosamine, the intensity of which is increased in comparison with the resonance signal located between 17 and 18 ppm, inclusive, in the ($^{13}$C) NMR spectrum of a pneumococcus type 5 capsular polysaccharide obtained after reductive amination, in the presence of sodium cyanoborohydride, at pH 8, for 48 hours; or
(ii) an HPAEC-PAD chromatogram which comprises a peak located immediately after the pneumosamine peak, characteristic of quinovosamine, the intensity of which is increased in comparison with the equivalent peak in the HPAEC-PAD chromatogram of a pneumococcus type 5 capsular polysaccharide obtained after reductive amination, in the presence of sodium cyanoborohydride, at pH 8, for 48 hours; or
(iii) both.

In other words, an aminated polysaccharide according to the invention, aminated on the terminal aldehyde group, essentially consists of repeating units of formula (II)

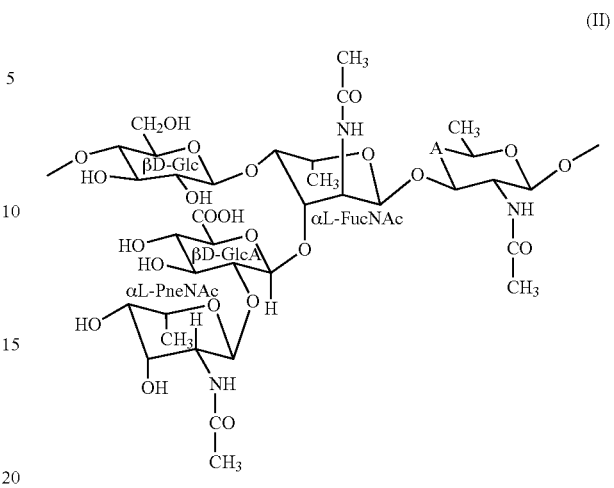

(II)

in which A is independently and randomly C=O or CHOH.

The expression "aminated polysaccharide essentially consisting" is intended to mean a polysaccharide aminated on the terminal aldehyde group in which the percentage of repeating units of formula (II) is at least 85%, preferably at least 90%, entirely preferably at least 95%.

Depending on the method used to produce the aminated polysaccharides according to the invention, the proportion of repeating units of formula (II) in which A is C=O (formula (II')) can vary considerably and, consequently, the same goes for the proportion of repeating units of formula (II) in which A is CHOH (formula (II")).

The second method according to the invention generates an aminated polysaccharide in which the repeating units correspond to formula (II") since, in NMR, the resonance signal corresponding to the Sug residue disappears in favor of the resonance signal corresponding to N-acetylated quinovosamine. The polysaccharide contains at least 95% of repeating units of formula (II").

On the other hand, using the first method according to the invention, an aminated polysaccharide is produced in which the units of formula (II')/units of formula (II") ratio is clearly different. Specifically, in NMR, the resonance signal corresponding to the Sug residue is visible, as is that corresponding to the N-acetylated quinovosamine. The polysaccharide contains from 85 to 95% of repeating units of formula (II').

As pointed out previously, a polysaccharide according to the invention can be aminated using various compounds. When the polysaccharide according to the invention is intended for the production of conjugates, the compound for aminating the polysaccharide is advantageously chosen according to the structure that it is hoped these conjugates will be given. In general, the conjugates according to the present invention correspond to the formula Ps-CH$_2$—NH—R in which: Ps denotes the pneumococcus type 5 capsular polysaccharide essentially consisting of repeating units of formula (II);
R is
 a carrier polypeptide P;
 a compound of formula (III) L—P, in which a carrier polypeptide is linked to a linking agent (L); or
 a compound of formula (III') S—L'—P, in which a carrier polypeptide P is linked to a spacer (S) via a linking agent (L');

C denotes the carbon atom of the terminal aldehyde group of the polysaccharide; and N denotes the nitrogen atom of the amine group provided by R.

The compounds P, L and S will be described later in the description, in the section devoted to the conjugates. It is, however, noted from hereon that these compounds must all of course comprise a free primary amine group capable of reacting with an aldehyde function. They may be used in each of the two methods according to the invention, without any distinction.

In the first method according to the invention, the reductive amination to which the polysaccharide is subjected consists in particular in reacting the polysaccharide with a compound comprising an amine function such as the compounds P, L or S, in the presence of a reducing agent selective for a Schiff base, such as cyanoborohydride or pyridine borane, under the conditions of pH and of temperature already specified, preferably between 30 min and 4 hours.

In order to obtain a degree of amination similar to that obtained under conventional conditions, an incubation time of between 2 and 4 hours, inclusive, is recommended. When the incubation time does not exceed 2 hours, the Sug compounds are not modified. Beyond 2 hours, reduced Sugs are observed, generally coexisting with unmodified Sugs in the polysaccharide chain. Consequently, the longer the incubation time, the greater the proportion of reduced Sug. Beyond 4 hours, the undesirable compound X is identified by NMR.

So as not to prolong the reductive amination reaction time beyond the required time, this reaction should be stopped by rapid methods, in particular by selective precipitation of the aminated polysaccharide. The aminated polysaccharide is, for example, purified by alcoholic precipitation when the aminated compound is a linking agent or a spacer. Precipitation with ammonium sulfate is preferred when the aminated compound is a polypeptide. The methods of purification by precipitation are conventional methods, well known to those skilled in the art.

In general, a buffered medium such as the citrate/phosphate buffer is used, but another buffer with a pKa of between 2.5 and 6 is also suitable. By way of example, a citrate, acetate or succinate buffer may be used. Buffers for which the chemical formula comprises compounds carrying an amino group, such as, for example, a glycine buffer are, however, excluded. The temperature of the reaction medium is generally between 4 and 70° C., depending on the aminated compound used, preferably between 20 and 50° C., and even more preferably between 20 and 37° C., when the aminated compound is a polypeptide.

For use in the first method according to the invention, the polysaccharide may be either native or fragmented beforehand. Any method of fragmentation may be suitable, on condition that it preserves the structural integrity of the native polysaccharide. The free- radical fragmentation method described later is most particularly suitable.

Although the weight ratios between the polysaccharide, the aminated compound and the cyanoborohydride are not critical, better yields of aminated polysaccharides are obtained in the range of polysaccharide/aminated compound/cyanoborohydride weight ratios ranging from 1/0.1/0.02 to 1/5/0.2 when a linking agent L or a spacer S is used as aminated compound; or in the range of weight ratios ranging from 1/0.2/0.02 to 1/1/0.2 when a carrier polypeptide is used as aminated compound. The optimum yields of aminated polysaccharides are obtained with a 1/1/0.1 ratio when the aminated compound is a linking agent or spacer or with a 1/0.5/0.1 ratio when the aminated compound is a carrier polypeptide.

For use in the second method according to the invention, the polysaccharide is preferably a native, nondepolymerized polysaccharide, since, for carrying out this second method, the polysaccharide is necessarily subjected to fragmentation, after reduction, so as to reintroduce terminal aldehyde groups.

In the second method according to the invention, the reduction of the polysaccharide is carried out conventionally, e.g. at ambient temperature, in aqueous medium, at basic pH, preferably at a pH of between 8 and 10. The strong reducing agent specific for the ketone and aldehyde functions is used in excess, e.g. at a molar concentration of at least 10 times, preferably of at least 100 times, greater than that of the polysaccharide. A borohydride, such as sodium borohydride, is a reducing agent of choice. The reaction time may be 30 min to 2 hours, preferably 1 hour.

The reduced polysaccharide can then be purified by any method, preferably by alcoholic precipitation. The depolymerization of the reduced polysaccharide can be carried out in particular by controlled hydrolysis. The oxidative free-radical depolymerization method as described in EP 562 107 is preferably used. The fragmented polysaccharides can then be purified conventionally, e.g. by alcoholic precipitation before the reductive amination step.

In the second method according to the invention, the reductive amination can be carried out under any conditions, including conventional conditions, since there is no longer any Sug compound in the structure of the reduced and fragmented polysaccharide and, consequently, no longer any risk of forming the undesirable compound X.

Thus, in the second method according to the invention, the reductive amination to which the polysaccharide is subjected simply requires reaction of the polysaccharide with a compound comprising an amine function, such as the compounds P, L or S, in the presence of a reducing agent selective for a Schiff base.

It is possible to use the conditions described for the first method according to the invention and, since, in this case, the incubation time and also the pH are no longer critical, with or without the time limitations or the restrictions relating to the pH range. Generally, under conventional conditions, the pH of the reaction medium is within a broad range of from 5 to 9, but a pH of between 5 and 8 is preferably chosen. An incubation time generally of between 2 hours and 48 hours gives good yields of aminated polysaccharide. The incubation temperature is generally between 20° C. and 50° C.

Once the reductive amination has been carried through to a successful conclusion, the aminated polysaccharide is purified from the reaction medium by means of usual methods, e.g. by alcoholic or ammonium sulfate precipitation, by dialysis, by exclusion-diffusion chromatography or by ultrafiltration, according to needs.

As previously mentioned; an aminated polysaccharide may already be a conjugate when the compound having reacted with the terminal aldehyde function of the polysaccharide is a carrier polypeptide. This conjugate has the formula Ps-CH$_2$—NH—P, in which the polysaccharide (Ps) is directly coupled to the carrier polypeptide (P).

For this reason, the subject of the invention is also:

a. A method for producing a conjugate according to the invention of formula (IV) Ps-CH$_2$—NH—P in which Ps denotes the pneumococcus type 5 capsular polysaccharide; according to which method the polysaccharide is reacted with a carrier polypeptide (P), in the presence of a reducing agent selective for a Schiff base, at a pH of 4 to 6.5, preferably of 5 to 6, for a period not exceeding 4 hours.
b. A method for producing a conjugate according to the invention of formula (IV) Ps-CH$_2$—NH—P in which Ps denotes the pneumococcus type 5 capsular polysaccharide; according to which method (i) the native polypeptide is reduced with a strong reducing agent specific for ketone and aldehyde functions, (ii) the reduced polysaccharide is fragmented, and (iii) the reduced and fragmented polysaccharide is subjected to a reductive amination in the presence of a carrier polypeptide P.
c. A method for producing a conjugate according to the invention of formula (V) Ps-CH$_2$—NH—L—P, according to which:
  (i) a pneumococcus type 5 capsular polysaccharide (Ps) is reacted with a linking agent (L) having at least one amine function, in the presence of a reducing agent selective for a Schiff base, a pH of 4 to 6.5, preferably of 5 to 6, for a period not exceeding 4 hours, in order to obtain an activated polysaccharide of formula (VI) Ps-CH$_2$—NH—L, and
  (ii) the activated polysaccharide is coupled to a carrier polypeptide (P) in order to obtain the conjugate of formula (V) Ps-CH$_2$—NH—L—P; or alternatively,
d. A method for producing a conjugate according to the invention of formula (V) Ps-CH$_2$—NH—L—P, according to which a pneumococcus type 5 capsular polysaccharide (Ps) is reacted with an activated carried polypeptide of formula (VII) L—P, in which L is a linking agent having at least one polyamine function and P is a carrier polypeptide, in the presence of a reducing agent selective for a Schiff base, at a pH of 4 to 6.5, preferably of 5 to 6, for a period not exceeding 4 hours, in order to obtain the conjugated formula (V) Ps-CH$_2$—NH—L—P.
e. A method for producing a conjugate according to the invention of formula (V) Ps-CH$_2$—NH—L—P, according to which:
  (i) a pneumococcus type 5 capsular polysaccharide (Ps) is reacted with an agent capable of reducing a ketone function,
  (ii) a reduced polysaccharide fragmented.
  (iii) the reducing fragmented polysaccharide is coupled, by reductive amination, with a linking agent (L) having at least one amine function, in order to obtain an activated polysaccharide of formula (VI) Ps-CH$_2$—NH—L, and the activated polysaccharide is coupled to a carrier protein (P), in order to obtain the conjugate of formula (V) Ps-CH$_2$—NH—L—P, or alternatively,
f. A method for producing a conjugate according to the invention of formula (V) Ps-CH2—NH—L—P, according to which:
  (i) a pneumococcus type 5 capsular polysaccharide (Ps) is reacted with an agent capable of reducing a ketone function,
  (ii) the reduced polysaccharide is fragmented, and
  (iii) the reduced and fragmented polysaccharide is coupled, by reductive amination, with an activated carrier polypeptide of formula (VII) L—P, in which L is a linking agent having at least one free amine function, in order to obtain the conjugate of formula (V) Ps-CH$_2$—NH—L—P.
g. A method for producing a conjugate according to the invention of formula (VIII) Ps-CH$_2$—NH—S—L'—P, according to which:
  (i) a pneumococcus type 5 capsular polysaccharide is reacted with a spacer (S) having at least one amine function, in the presence of a reducing agent selective for a Schiff base, at a pH of 4 to 6.5, preferably of 5 to 6, for a period not exceeding 4 hours, in order to obtain a derivatized polysaccharide of formula (IX) Ps-CH$_2$—NH—S,
  (ii) the derivatized polysaccharide is coupled with a linking agent (L'), in order to obtain an activated polysaccharide of formula (X) Ps-CH$_2$—NH—S—L', and
  (iii) the activated polysaccharide is coupled with a carrier polypeptide (P), in order to obtain a conjugate of formula (VIII) Ps-CH$_2$—NH—S—L'—P; or alternatively,
h. A method for producing a conjugate according to the invention of formula (VIII) Ps-CH$_2$—NH—S—L'—P, according to which:
  (i) a pneumococcus type 5 capsular polysaccharide is reacted with a spacer (S) having at least one amine function, in the presence of a reducing agent selective for a Schiff base, at a pH of 4 to 6.5, preferably of 5 to 6, for a period not exceeding 4 hours, in order to obtain a derivatized polysaccharide of formula (IX) Ps-CH$_2$—NH—S, and
  (ii) the derivatized polysaccharide is coupled with an activated carrier polysaccharide of formula (XI) L'—P, in which L' is a linking agent and P is a carrier polypeptide, in order to obtain the conjugate of formula (VIII) Ps-CH$_2$—NH—S—L'—P.
i. A method for producing a conjugate according to the invention of formula (VIII) Ps-CH$_2$—NH—S—L'—P, according to which:
  (i) a pneumococcus type 5 capsular polysaccharide (Ps) is reacted with an agent capable of reducing a ketone function,
  (ii) the reduced polysaccharide is fragmented,
  (iii) the reduced and fragmented poiysaccharide is coupled, by reductive amination, to a spacer (S) carrying at least one amine function, in order to obtain a derivatized polysaccharide of formula (IX) Ps-CH$_2$—NH—S,
  (iv) the derivatized polysaccharide is coupled to a linking agent (L'), in order to obtain an activated polysaccharide of formula (X) Ps-CH$_2$—NH—S—L', and
  (v) the activated polysaccharide is coupled to a carrier polypeptide (P), in order to obtain the conjugate of formula (VIII) Ps-CH$_2$—NH—S—L'—P; or alternatively,
j. A method for producing a conjugate according to the invention of formula (VIII) Ps-CH$_2$—NH—S—L'—P, according to which:
  (i) a pneumococcus type 5 capsular polysaccharide (Ps) is reacted with an agent capable of reducing a ketone function,
  (ii) the reduced polysaccharide is fragmented,
  (iii) the reduced and fragmented polysaccharide is coupled, by reductive amination, to a spacer (S) carrying at least one amine function, in order to obtain a derivatized polysaccharide of formula (IX) Ps-CH$_2$—NH—S, and
  (iv) the derivatized polysaccharide is coupled with an activated carrier polypeptide of formula (XI) L'—P, in which L' is a linking agent and P is a carrier polypeptide, in order to obtain the conjugate of formula (VIII) Ps-CH$_2$—NH—S—L'—P.

In its most general scope, the term "carrier polypeptide (P)" denotes a chain of amino acids, whatever its size, and the post-translational modifications which could have occurred, comprising at least one "T-helper" epitope. Since it is known that a T-helper epitope can consist of 10-15 amino acids, the term "carrier polypeptide" encompasses peptides. Of course, it also encompasses proteins.

The term "T-helper epitope" is intended to mean a chain of amino acids which, in the context of one or more MHC molecules, activates T-helper lymphocytes. The carrier polypeptide of the conjugate causes the development of T-dependent immunity specific for the pneumococcus type 5 polysaccharide, with production of specific antibodies against the polysaccharide, subsequent to the administration of the conjugate. It also induces an increase in the specific antibody titer at the time of a booster immunization.

For use in the conjugates according to the invention, the carrier polypeptide may be a bacterial toxoid obtained by chemical detoxification, such as tetanus toxoid, or obtained by genetic mutation, such as diphtheria toxoid (CRM 197, by way of example), *Pseudomonas aeruginosa* exoprotein A or *Staphylococcus aureus* exotoxin A. It is also possible to use the outer membrane proteins of bacteria, such as the OMP1 or OMP2 proteins of *Neisseria meningitidis;* the lambB, OmpC, OmpaA, OmpF and PhoE proteins of *Escherichia coli*, the CotC or CotD protein of *Bacillus subtilis*, bacterial porins such as *Neisseria meningitidis* B Class 1 porin or *Klebsiella pneumoniae* porin P40; also lipoproteins such as *Borelia burgdorfi* OspA, *Streptococcus pneumoniae* PspA, *Neisseria meningitidis* Transferrin binding protein type 2 (TBP2), *Escherichia coli* TraT, *Streptococcus pneumoniae* adhesin A. Proteins of viral origin, such as influenza virus hemagglutinin can also play the role of carrier polypeptide, as can the p24E, p24N, p24M and p24H peptides described in WO 94/29339, carrying a T-helper epitope, or the PADRE (PanDR T-helper epitope) peptides described by Del guercio et al. (Vaccine (1997), Vol. 15/4, p. 441-448).

The production of the conjugates of formula (IV) Ps-CH$_2$—NH—P is carried out in a single step, the reaction of reductive amination of the polysaccharide also providing the conjugation of the polysaccharide to the polypeptide. On the other hand, the production of the conjugates of formula (V) Ps-CH$_2$—NH—L—P or (VIII) Ps-CH$_2$—NH—S—L—P is carried out in several different steps, the first step consisting of the implementation of one of the two methods for producing an aminated polysaccharide according to the invention, resulting in the reductive amination of the polysaccharide with the compound L or S.

The spacer S and the linking agents L and L' are compounds having at least two functional groups arranged within the compound in relatively opposite directions. As regards the spacer S and the linking agent L, one of the functional groups should be capable of reacting with the terminal aldehyde of the polysaccharide during the reductive amination, the other being respectively capable of reacting with a linking agent L' or with a carrier polypeptide. As regards the linking agent L', one of the functional groups should be capable of reacting with the spacer, the other being capable of reacting with a carrier polypeptide.

For the purposes of the present invention, the linking agent L is a compound of the formula (XII) R1-A-R2, in which:

A denotes an aliphatic and/or aromatic chain which may be substituted or unsubstituted, saturated or unsaturated;

R1 denotes a primary amine or a chemical radical carrying a primary amine, such as, for example, the radical hydrazide, NH$_2$—NH—CO; and R2 denotes a functional group capable of reacting with a functional group of the carrier polypeptide.

Advantageously, A denotes an alkyl, an alkylene or a dithioalkyl, comprising from 1 to 12, advantageously from 2 to 8, preferably from 2 to 6, carbon atoms.

Advantageously, R2 is capable of reacting with a carboxyl, thiol or amine group. Thus, R2 can be, independently of R1, an amine group or a radical carrying an amine group, such as the radical hydrazide. R2 can also be a thiol or carboxyl group.

Thus, a compound of formula R1-A-R2 can be an alkyl dihydrazide such as adipic acid dihydrazide; a monoamino thioalkyl such as cysteine or cysteamine, or a diamino thioalkyl such as cystamine; a diaminoalkyl or diaminoalkylene, such as diaminomethane, diaminoethane or diaminohexane.

For the purposes of the present invention, the spacer S is a compound of formula (XIII) R1-A-R2', in which:

A denotes an aliphatic and/or aromatic chain which may be substituted or unsubstituted, saturated or unsaturated;

R1 denotes a primary amine or a chemical radical carrying a primary amine, such as, for example, the radical hydrazide, NH$_2$—NH—CO; and R2' denotes a functional group capable of reacting with a functional group of a linking agent L'.

According to a particular mode, the spacer S can be chosen from the compounds of formula (XII) R1-A-R2.

For the purposes of the present invention, the choice of the linking agent L' is conditioned firstly by the functional group R2' carried by S, then by the functional group of the carrier polypeptide which must intervene in the conjugation operation. The linking agent L' is a compound of formula (XIV) R3-B-R4, in which:

B denotes an aliphatic and/or aromatic chain which may be substituted or unsubstituted, saturated or unsaturated;

R3 denotes a functional group capable of reacting with the functional group R2'; and R4 denotes a functional group capable of reacting with a functional group of the carrier polypeptide.

Advantageously, B denotes an alkyl or an alkylene which may be substituted or unsubstituted, comprising from 1 to 12, preferably from 2 to 8, carbon atoms; an aryl, an alkylaryl or an arylalkylene, comprising from 7 to 12 carbon atoms; a phenyl or phenylene which may be substituted or unsubstituted.

When R2' is a thiol group, R3 can be a thiol group; an unsaturated (α- or β-carbonyl or an imidyl group, in particular a maleimidyl group; an acyl halide or an alkyl halide, in which the halogen is a bromine, a chlorine or an iodine.

Advantageously, R4 is capable of reacting with a carboxyl, thiol or amine group. Thus, if the functional group of the carrier polypeptide which must intervene in the conjugation operation is a thiol, R4 can be a maleimide group. Similarly, if the functional group of the carrier polypeptide which must intervene in the conjugation operation is an amine, R4 can be a carboxyl group or preferably an N-hydroxysuccinimidyl or N-hydroxysulfosuccinimidyl group.

When the spacer S is an aminothiol such as cysteine, cysteamine or cystamine, the linking agent L' is advantageously a succinimidyl maleimidyl alkyl. The latter may in particular be γ-maleimidobutyric acid N-hydroxysuccinimide ester or N-sulfosuccinimide ester (GMBS or sulfo-GMBS), ε-maleimidocaproic acid N-hydroxysuccinimide ester (MCS), succinimidyl 4-(p-maleimidophenyl) butyrate (SMPB) or sulfo-succinimidyl 4-(p-maleimidophenyl) butyrate (sulfo-SMPB), maleimidobenzoic acid N-hydroxysuccinimide ester (MBS) or maleimidobenzoic acid N-hydroxysulfosuccinimide ester (sulfo-MBS), 4-(N-maleimidomethyl)-cyclohexanecarboxylic acid N-hydroxysuccinimide ester (SMCC) or 4-(N-maleimidomethyl)cyclohexanecarboxylic acid N-hydroxysulfosuccinimide ester (sulfo-SMCC).

When the spacer S is a diaminoalkyl or a dihydrazide, the linking agent L' is advantageously chosen from the disuccinimidylalkyl or succinimidylmaleimidoalkyl compounds of formula (XIV) R3-B-R4 in which B is an alkyl group, R3 is a succinimidyl group and R4 is a succinimidyl or maleimido group.

The disuccinimidyl group can be disuccinimidyl suberate (DSS), bis(sulfosuccinimidyl) suberate (BS3), disuccinimidyl glutarate (DSG), the succinimidyl diester of adipic acid (SIDEA) or the succinimidyl diester of succinic acid. The succinimidyl and or sulfosuccinimidyl groups are capable of reacting with an amine group. The succinimidylmaleimidoalkyl compound can be one of those mentioned above.

In the methods of conjugation a. to j., the steps of derivatization, of activation and of conjugation per se can be carried out according to procedures well known to those skilled in the art. They are in particular described in the reference work entitled Bioconjugate Techniques (1996) Ed Academic press. By way of example, reference is made to this work to indicate that conjugation reactions using an amine group and a carboxyl group are advantageously carried out in the presence of a carbodiimide.

The steps of derivatization, of activation and of conjugation have no effect on the chemical structure of the repeating units of the polysaccharide.

The conjugates obtained according to one of the methods a. to j. can be finally purified, e.g. by ammonium sulfate precipitation, by ultrafiltration, by exclusion-diffusion chromatography or by partition chromatography, in order to remove the residual, unconjugated polysaccharide and protein fractions.

The subject of the invention is also a pharmaceutical composition for therapeutic or prophylactic use, comprising a polysaccharide according to the invention, preferably in the form of a conjugate. The latter can be formulated with a pharmaceutically acceptable diluent or support, e.g. a phosphate buffer, and, where appropriate, a lyophilization excipient. In general, these products can be selected as a function of the method and the route of administration and according to the standard pharmaceutical practices. The suitable diluents, and also that which is essential in developing a pharmaceutical composition, are described in *Remington's Pharmaceutical Sciences*, which serves as a standard reference in this field. The composition can also contain an adjuvant, e.g. an aluminum hydroxide, an aluminum phosphate or an aluminum hydroxyphosphate. A preserving agent such as phenoxyethanol formol can also be used. An immunization dose can be prepared in a volume of 0.1 ml to 2 ml, preferably in a volume of 0.5 ml. By way of example, it is indicated that a dose can contain 0.475 mg of $PO_4^{2-}$ ion, 4.5 mg of sodium chloride and optionally 300 µg of $AL^{3+}$ ions. The immunization composition according to the invention may also be combined with other immunization antigens, in particular pneumococcus polysaccharide antigens, which may or may not be conjugated to a polypeptide carrier. A multivalent vaccine against pneumococcus is then obtained, in which the pneumococcus type 5 polysaccharide is in one of the forms described in the invention.

A subject of the invention is also a method of treatment or prevention against the pneumococcus type 5 infections, which consists in administering, to infants, young children, adults or elderly individuals, a sufficient dose of a composition according to the invention, optionally adjuvanted, so as to induce a protective specific immune response against this pathogen. The method is carried out by administration of at least one immunization dose of the composition according to the invention. For example, between 1 and 3 injections may be given, but preferably 3 injections are given, leaving a period of one month between each injection. A composition according to the invention may be administered by any conventional route of use in the vaccine field, in particular systemically, i.e. parenterally, e.g. subcutaneously, intramuscularly, intradermally or intravenously; or mucosally, e.g. orally or nasally. The amount administered takes into account the carrier polypeptide used for the route of administration. By way of example, the dose of polysaccharide required contained in the conjugate in order to observe protective immunity against serotype 5 subsequent to parenteral administration is generally between 0.5 µg and 10 µg, but preferentially between 0.5 and 5 µg, and even more preferably between 0.5 µg and 2 µg, when the carrier protein is the tetanus toxoid. In an unconjugated form, the dose of polysaccharide required is between 10 and 50 µg, preferably between 20 and 30 µg.

The present invention will be more clearly understood in light of the following examples which serve to illustrate the invention without, however, limiting the contents thereof.

FIG. 1 represents the NMR spectra of a polysaccharide aminated according to various methods of production.

The first spectrum is that of the fragmented pneumococcus type 5 polysaccharide after oxidative free-radical depolymerization. In the region of the high fields of the spectrum, the resonance signals of the methyl carbons of the 3 N-acetylated hexosamines of the repeating unit of the polysaccharide: N-acetylated fucosamine (C6 FucNAc), N-acetylated pneumosamine (C6 pneNAc) and Sug (C6 Sug), are identified.

The second spectrum is that of the aminated polysaccharide obtained according to the second method which is the subject of the invention. The disappearance of the signal corresponding to Sug (C6 Sug) and the appearance of a new signal corresponding to N-acetylated quinovosamine (C6 QuiNAc), are observed.

The third spectrum is that of the aminated polysaccharide obtained according to the first method which is the subject of the invention. It is identical to the NMR spectrum of the fragmented, nonaminated polysaccharide.

The fourth spectrum is that of the polysaccharide aminated under conventional conditions. The presence of two additional signals in the region of the high fields of the spectrum is noted, corresponding to N-acetylated quinovosamine and to the compound X and also a decrease in the height of the signal corresponding to Sug.

FIG. 2 represents the chromatogram obtained by HPAEC-PAD of the depolymerized native polysaccharide (curve with continuous line), of the polysaccharide aminated according to the conventional method of reductive amination (the en-dashed curve), according to the first method which is the subject of the invention (dashed curve) or according to the second method which is the subject of the invention (curve with dashes and dots).

EXAMPLE 1

Reductive Amination at pH 6, for 2 Hours, of the Pneumococcus Type 5 Capsular Polysaccharide, After Fragmentation a) Free-radical Depolymerization of the Native Pneumococcus Type 5 Polysaccharide The polysaccharide at a concentration of 2.5 mg/ml in aqueous solution is fragmented with ascorbic acid, ferrous sulfate and also cupric sulfate. The number-amount of mmol of ascorbic acid is one hundred times greater than that of the ferrous sulfate and of the cupric sulfate. The weight ratio of ascorbic acid to the polysaccharide is 0.1. The reaction mixture is incubated in a water bath at 30° C. in the dark for 1 hour 30 min. The hydrolyzed polysaccharide is purified by precipitation in 80% ethanol, followed by centrifugation. The centrifugation pellet is dialyzed and then lyophilized. The average size of the fragmented polysaccharide is approximately 30-35 repeating units, as measured by exclusion chromatography with triple detection (Viscoteck).

b) Reductive Amination of the Polysaccharide

The fragmented polysaccharide is redissolved in a citrate/phosphate, 0.2 M buffer, pH 6, at a concentration of 10 mg/ml in the presence of diaminohexane (DAH) hydrochloride (Aldrich) and sodium cyanoborohydride ($NaCNBH_3$) (Sigma). The polysaccharide/DAH hydrochloride and $NaCNBH_3$/DAH hydrochloride weight ratios are, respectively, 0.8 and 0.1. The reaction mixture is incubated at 50° C. in a water bath for 2 hours. The reaction is then stopped by precipitation of the aminated polysaccharide in 80% ethanol, followed by centrifugation. The precipitation pellet is then taken with 0.5 M NaCl, in a proportion of 10 mg/ml of polysaccharide, and then subjected to 8 successive dialysis baths (first 4 baths carried out in a 0.5 M NaCl solution, followed by 4 baths carried out in ultrafiltered water). The derivatized and thus aminated polysaccharide is finally lyophilized.

EXAMPLE 2

Reductive Amination of the Pneumococcus Type 5 Capsular Polysaccharide, After Reduction and Fragmentation a) Reduction and Fragmentation of the Native Polysaccharide 10 mg/ml of sodium borohydride ($NaBH_4$), are added to 10 ml of an aqueous solution of native polysaccharide at 10 mg/ml, adjusted to pH 9±0.5 with 1 N aqueous ammonia, and then the reaction mixture is left at ambient temperature for 2 hours in the dark. The $NaBH_4$ is then destroyed by adding a few drops of glacial acetic acid. The reduced polysaccharide is subsequently dialyzed against water, and is then fragmented using the protocol described in paragraph a) in Example 1. A polysaccharide containing on average 30-35 repeating units is obtained. The reduced and fragmented polysaccharide is subsequently lyophilized.

b) Reductive Amination of the Reduced and Fragmented Polysaccharide

The reduced and fragmented polysaccharide is redissolved in a 0.2 M phosphate buffer, pH 7.5, at a concentration of 10 mg/ml in the presence of diaminohexane (DAH) hydrochloride and sodium cyanoborohydride ($NaCNBH_3$) prepared extemporaneously. The polysaccharide/DAH hydrochloride and $NaCNBH_3$/DAH hydrochloride weight ratios are, respectively, 0.8 and 0.1. The reaction mixture is incubated at 50° C. in a water bath for 48 to 72 hours. The aminated polysaccharide is then purified by precipitation in 80% ethanol, followed by centrifugation. The precipitation pellet is taken up with 0.5 M NaCl, in a proportion of 10 mg/ml of polysaccharide, and then subjected to 8 successive dialysis baths (first 4 baths carried out in a 0.5 M NaCl solution, followed by 4 baths carried out in ultrafiltered water). The derivatized and thus aminated polysaccharide is finally lyophilized.

EXAMPLE 3

Production and Study of the Immunogenic Capacity of the Conjugates Obtained Using the Derivatized and Aminated Polysaccharides of Examples 1 and 2 a) Production of the Conjugates

The aminated polysaccharides of Examples 1 and 2 are conjugated to tetanus toxoid (TT) via DSS. Initially, the aminated polysaccharide is activated with DSS, and then the tetanus toxoid is conjugated to the activated polysaccharide.

The aminated polysaccharide of Example 1 or 2 is taken up in aqueous solution at a concentration of 40 mg/ml. The DSS is taken up in a solution of DMSO in a proportion of 5 mg/ml. 2.5 ml of an aqueous solution of the aminated polysaccharide are added, dropwise, to 10 ml of the solution of DSS, with stirring. After incubation for 1 h 30, the reaction is stopped by precipitation in 50 ml of acetone. The precipitate is recovered by filtration over a buchner No. 5, which is then washed 5 times with 20 to 50 ml of acetone. The precipitate is then dried under vacuum and then under a stream of nitrogen.

The precipitate containing the derivatized polysaccharide is taken up with an appropriate volume of a solution of tetanus toxoid at 10 mg/ml in a 0.2 M phosphate buffer, such that the derivatized polysaccharide to tetanus toxoid weight ratio is between 1 and 2. The mixture is incubated at laboratory temperature, with stirring, for 16 to 20 hours. The reaction is then stopped by precipitation with 70% ammonium sulfate after 4-fold dilution of the mixture in a 0.2 M phosphate buffer. The medium containing the precipitate is stirred for 1 hour at laboratory temperature and then for 4 to 20 hours at +40° C. After having recovered the precipitate by centrifugation, it is finally taken up and dissolved in a 0.2 M phosphate buffer. The solution of the conjugate is obtained in a virtually pure form. The amounts of unconjugated tetanus toxoid and unconjugated polysaccharide are negligible. The solution is finally adjusted to the desired concentration with a view to use for immunization. The polysaccharide/protein ratio in the conjugate is 1/5.

b) Study of the Immunogenic Capacity of the Conjugates

The immunogenic capacity of the conjugates thus obtained is compared with that of a conjugate making use of a pneumococcus type 5 capsular polysaccharide subjected beforehand to a conventional reductive amination, described as follows: the native polysaccharide is first of all fragmented by free-radical depolymerization according to the procedure of paragraph a) of Example 1. A depolymerized polysaccharide containing 30-35 repeating units is obtained. The fragmented polysaccharide is then subjected to a reductive amination accord ng to the procedure of paragraph b) of Example 2. The aminated polysaccharide is then conjugated to tetanus toxoid via DSS under the operating conditions of paragraph a) of Example 3. The conjugate thus obtained has the same characteristics of purity and can be used as a vaccine. The polysaccharide/protein ratio in the conjugate is 1/5.

Fifteen NZB rabbits divided up into 3 different groups are injected intramuscularly on days D1 and D23 with one of the 3 polysaccharide conjugates, in a proportion of 0.5 µg of polysaccharide and 2.5 µg of tetanus toxoid per rabbit and per injection. Group 1 is immunized with the conjugate obtained using the aminated polysaccharide of Example 1, group 2 with the conjugate obtained using the aminated polysaccharide of Example 2, group 3 with the conjugate obtained using the polysaccharide aminated according to a conventional method, as described in the preceding paragraph of the present example. A group of "control" rabbits is injected intramuscularly with physiological saline on D1 and D23.

Blood samples are taken on D1, D23 and D36 in order to control these titers of serum antibodies specific for the pneumococcus type 5 polysaccharide, by ELISA on microplates coated with native pneumococcus type 5 polysaccharide (1 µg/microwell). The antibody titers contained in each rabbit are defined as being the inverse of the serum dilution which gives an optical density of 1 on a spectrophotometer subsequent to the developing of the ELISA assay using a colored indicator, trimethylbenzidine. The results are given in Table I below:

| Group | D1 | D23 | D36 |
| --- | --- | --- | --- |
| 1 | <10 | 239* (122-469)** | 2824 (1758-4535) |
| 2 | <10 | 110 (74-164) | 2929 (1180-7270) |
| 3 | <10 | 57 (29-113) | 423 (166-1078) |
| Control | <10 | <20 | <20 |

*represents the geometric mean of the specific serum antibody titers of 5 rabbits
**indicates the value of the lowest antibody titer and the value of the highest antibody titer in each group.

After two immunizations, the mean values of the specific antibody titers of the rabbits immunized with conjugates obtained using the aminated polysaccharides of Examples 1 and 2 are approximately 5 times higher than that of the rabbits immunized with the conjugates obtained using a polysaccharide aminated according to a conventional method of reductive amination.

When the polysaccharide/tetanus toxoid weight ratios are varied within a range of from 1/0.5 to 1/5, the results which are obtained in the previously described assays are similar in all respects.

The functionality of these antibodies is controlled using an opsonophagocytosis assay. The opsonizing titer is defined as being the inverse of the serum dilution which makes it possible to kill 50% of the bacteria.

The results are given in Table II below:

| Group | D1 | D23 | D36 |
|-------|------|---------|--------------|
| 1 | n.t. | 7* (3-18)** | 128 (27-599) |
| 2 | n.t. | 2 (2-3) | 185 (60-565) |
| 3 | n.t. | 2 (1-5) | 35 (11-110) |
| Control | n.t. | n.t. | n.t. |

*represents the geometric mean of the opsonizing titers of the 5 rabbits
**indicates the value of the lowest opsonizing titer and the value of the highest opsonizing titer in each group.
n.t.: not titered The opsonizing titers correlate with the titers of serum antibodies specific for the type 5 pneumococcus polysaccharide.

We claim:

1. A pneumococcus type 5 capsular polysaccharide, wherein the polysaccharide is aminated on the terminal aldehyde group and exhibits
   (i) a carbon (13C) NMR spectrum having
      (a) no resonance signal between 13 and 14 ppm inclusive;
      (b) no resonance signal between 11.5 and 12.5 ppm, inclusive; and
      (c) a resonance signal located between 17 and 18 ppm inclusive,
   characteristic of N-acetylated quinovosamine, the intensity of which is increased in comparison with the resonance signal located between 17 and 18 ppm, inclusive, in the (13C) NMR spectrum of a pneumococcus type 5 capsular polysaccharide obtained after reductive amination in the presence of sodium cyanoborohydride at pH 8 for 48 hours;
   (ii) an HPAEC-PAD chromatogram obtained by elution from a anion-exchange column in an 18 mM sodium hydroxide solution at a flow rate of 1 ml/min for 15 min of monosaccharides derived from hydrolysis of said polysaccharide having:
      (a) no peak between fucosamine and pneumosamine peaks; and
      (b) a peak located immediately after the pneumosamine peak characteristic of quinovosamine, the intensity of which is increased in comparison with the equivalent peak in the HPAEC-PAD chromatogram of a pneumococcus type 5 capsular polysaccharide obtained after reductive amination in the presence of sodium cyanoborohydride at pH 8 for 48 hours;
   or
   (iii) both, and wherein the anion-exchange column consists of a support based on polystyrene and sulfonated divinylbenzene having a degree of cross-linking of 55% and latex microbeads with quaternary ammonium groups; wherein the latex microbeads have a degree of cross-linking of 5% and the diameter of 400 nm.

2. A pneumococcus type 5 capsular polysaccharide which is aminated on the terminal aldehyde group, consisting of repeating units in which at least 95% of the repeating units are of formula II″

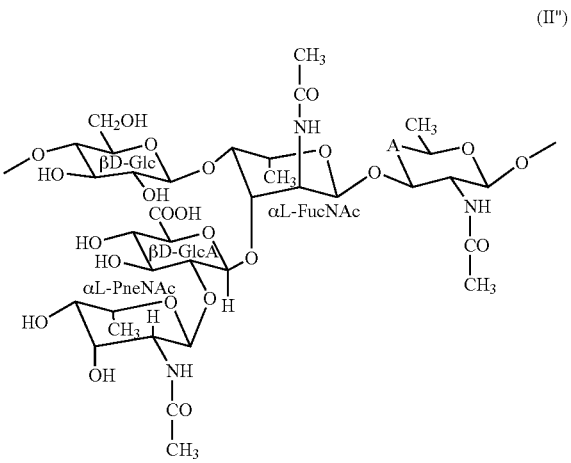

in which A is CHOH.

3. A polysaccharide-polypeptide conjugate comprising a polysaccharide according to claim 1 coupled to a carrier polypeptide (P).

4. A method for producing an aminated pneumococcus type 5 capsular polysaccharide according to claim 2, the method comprising (i) reacting a pneumococcus type 5 capsular polysaccharide with an agent for reducing a ketone function, (ii) fragmenting the reduced polysaccharide, and (iii) reductively aminating the reduced and fragmented polysaccharide.

5. The method according to claim 4 in which the polysaccharide which is reacted with the agent capable of reducing a ketone function is in native form.

6. The method according to claim 4 in which the agent capable of reducing a ketone function is NaBH$_4$.

7. The method according to claim 4 in which the reduced polysaccharide is fragmented by oxidative free-radical depolymerization.

8. The method according to claim 4 wherein the reductive amination of the reduced and fragmented pneumococcus type 5 capsular polysaccharide (Ps) is conducted with a carrier polypeptide (P), wherein the Pneumococcus type 5 capsular polysaccharide produced is a conjugate of formula Ps-CH$_2$-NH-P.

9. The method according to claim 4 wherein:
   (i) (a) the reductive amination is conducted with a linking agent (L) having at least one free amine function so as to form an aminated and activated polysaccharide of formula Ps-CH$_2$-NH-L, and
      (b) further comprising coupling the activated polysaccharide to a carrier polypeptide (P) in order to obtain an aminated pneumococcus type 5 polysaccharide of formula Ps-CH$_2$-NH-L-P; or, alternatively,
   (ii) the reductive amination is conducted with an activated carrier polypeptide of formula L-P, wherein L is a linking agent having at least one free amine function, in order to obtain an aminated pneumococcus type 5 polysaccharide of formula Ps-CH$_2$-NH-L-P.

10. The method according to claim 4, wherein:
   (i) the reductive amination is conducted with a spacer (S) having at least one free amine function so as to form an aminated and derivatized polysaccharide of formula Ps-CH$_2$-NH-S, and further comprising (ii) (a) coupling the derivatized polysaccharide with a linking agent (L') in order to obtain an activated polysaccharide of formula Ps-CH$_2$-NH-S-L', then the activated polysaccharide is coupled with a carrier polypeptide (P), in order to obtain an aminated pneumococcus type 5 polysaccharide of formula Ps-CH$_2$-NH-S-L'-P; or, alternatively, (b) coupling the derivatized polysaccharide with an activated carrier polypeptide of formula L'-P, wherein L' is a linking agent, in order to obtain an aminated pneumococcus type 5 polysaccharide of formula Ps-CH$_2$-NH-S-L'-P.

11. A pharmaceutical composition comprising a conjugate according to claim 3.

12. A pharmaceutical composition comprising a conjugate obtained by reducing ketone and aldehyde functions of a pneumococcus type 5 capsular polysaccharide, fragmenting the reduced polysaccharide, and subjecting the reduced and fragmented polysaccharide to a reductive amination in the presence of a reducing agent selective for a Schiff base, wherein the pneumococcus type 5 capsular polysaccharide (Ps) is coupled by the reductive amination to a carrier polypeptide (P) to yield the conjugate.

* * * * *